US005720275A

United States Patent [19]
Patil et al.

[11] Patent Number: 5,720,275
[45] Date of Patent: Feb. 24, 1998

[54] TRACHEAL GUIDE

[75] Inventors: Vijayalakshmi Patil, Fayetteville, N.Y.; Jeffrey C. Mullins, Ellettsville, Ind.

[73] Assignees: The Research Foundation of State Univ. of New York, Albany, N.Y.; Cook Incorporated, Bloomington, Ind.

[21] Appl. No.: 623,322

[22] Filed: Mar. 26, 1996

[51] Int. Cl.⁶ .................................................. A61M 16/00
[52] U.S. Cl. ........................ 128/200.26; 128/200.24; 128/207.14; 128/207.15; 128/911; 128/912; 128/DIG. 26
[58] Field of Search ................... 128/200.26, 200.24, 128/207.14, 207.15, 911, 912, DIG. 26

[56] References Cited

U.S. PATENT DOCUMENTS

| | | | |
|---|---|---|---|
| 4,063,561 | 12/1977 | McKenna. | |
| 4,454,887 | 6/1984 | Krüger. | |
| 4,509,514 | 4/1985 | Brain. | |
| 4,612,927 | 9/1986 | Krüger. | |
| 4,683,879 | 8/1987 | Williams | 128/200.26 |
| 4,832,020 | 5/1989 | Augustine | 128/207.14 |
| 4,848,331 | 7/1989 | Northway-Meyer | 128/207.14 |
| 4,995,388 | 2/1991 | Brain. | |
| 5,038,766 | 8/1991 | Parker. | |
| 5,323,771 | 6/1994 | Fisher et al. | 128/200.26 |
| 5,339,805 | 8/1994 | Parker | 128/200.26 |

Primary Examiner—Vincent Millin
Assistant Examiner—William J. Deane, Jr.
Attorney, Agent, or Firm—Richard J. Godlewski

[57] ABSTRACT

A tracheal guide (10) for positioning a medical device (11) such as an endotracheal or intubation tube in the trachea (12) of a human patient (13). The tracheal guide includes an elongated member (14) with a generally U-shaped passage (17) extending therethrough. Ears (18, 33) are disposed laterally about the passage and, in particular, the distal end (15) thereof. These ears are shaped for conformance with and placement in the piriform fossa (19, 34), which are located in the vicinity of the glottic opening (39) of the trachea. A tongue (25) extends distally from the distal end of the elongated member and into the esophagus (32) of the patient when the ears of the guide are positioned in the piriform fossa. The passage of the elongated member includes first and second surfaces (20, 24) that form an edge (26) that extends anterior to the cricoid cartilage and, in particular, the transverse arytenoid when the edge and ears are properly positioned in the patient's airway. These passage surfaces atraumatically guide an endotracheal or intubation tube directly into the trachea (12) and without concern of undesired entry into the esophagus. These surfaces are selected to have particular angles (21, 24) with respect to the outer reference surface (30) of the elongated member so as to accommodate most human patients.

20 Claims, 7 Drawing Sheets

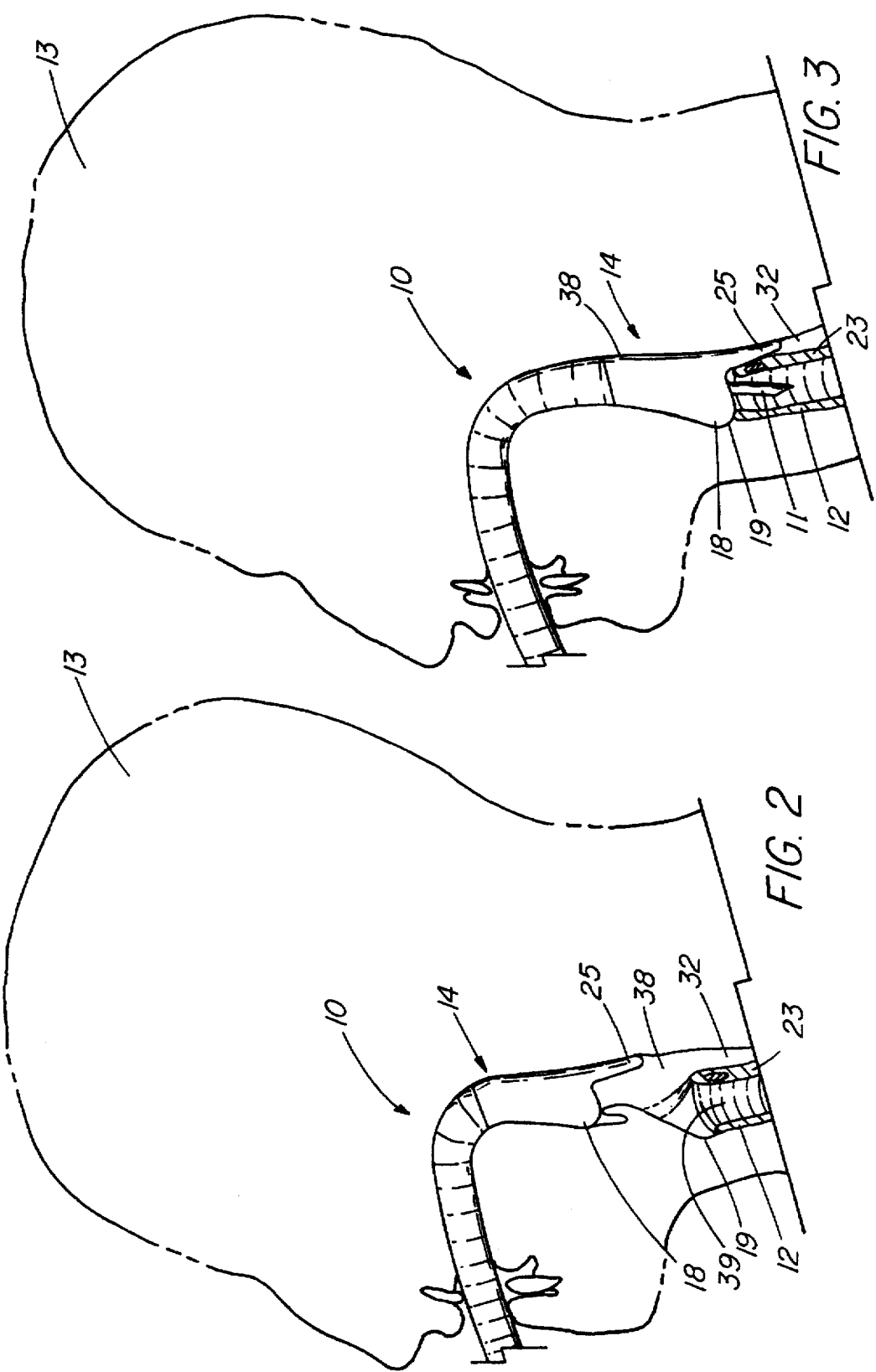

TRACHEAL GUIDE

TECHNICAL FIELD

This invention is directed generally to medical devices and, in particular, to a guide for positioning medical devices in the trachea of a human patient.

BACKGROUND OF THE INVENTION

Emergency medical technicians or emergency room personnel are often faced with having to intubate a patient in an emergency situation where time is of the essence. Failure to intubate the patient within just a few minutes can cause oxygen deprivation and permanent brain damage. Emergency room physicians, anesthesiologists and pulmonologists have extensive training in quickly and accurately positioning an endotracheal tube or other intubation device into the trachea of the patient. Even so, these medical personnel are concerned about clearing the patient's airway and inserting the intubation tube directly into the trachea of the patient rather than the esophagus. Inserting the intubation tube into the esophagus merely inflates the patient's stomach and further delays intubating the patient.

Often a trying experience for even the most qualified physicians, an intubation procedure can be even more exasperating for minimally trained medical personnel. Several prior art devices have been developed for assisting these medical personnel for guiding an intubation tube directly into the trachea of a patient. However, the distal end of these devices is at best marginal for accurately positioning the distal end of the guide at the glottic opening of the patient's trachea. Furthermore, various of these prior art devices use balloon inflatable collars to block off the entrance to the esophagus. These inflatable collars require even more time for placement of the guide, which in turn subjects the patient to further delay and consequent brain damage. As a result, these prior art devices are deficient in providing a guide which is readily and quickly positioned in the airway of the patient for guiding an intubation tube or other device into the patient's trachea.

SUMMARY OF THE INVENTION

The foregoing problems are solved and a technical advance is achieved in an illustrative embodiment of a tracheal guide for positioning a medical device such as an endotracheal tube directly into the trachea of a human patient without concern for inadvertently directing the device into the esophagus. This tracheal guide is advantageous for medical personnel who do not have extensive training in intubating patients in emergency situations. The tracheal guide comprises an elongated member having a passage extending longitudinally therethrough. First and second ears are disposed about the distal end of the member and are shaped for conformance with and placement in the piriform fossa of a human patient. These ears readily position the guide in the airway of the patient for nearly foolproof intubation of the patient. A first surface extending longitudinally in the passage of the elongated member is inclined at a predetermined angle with respect to an outer reference surface of the guide so as to direct a medical device such as an endotracheal tube directly into the trachea of the patient without traumatizing the cricoid cartilage and, in particular, the transverse arytenoid. This first surface is inclined toward the distal end of the elongated member and in a direction anterior of the cricoid cartilage of the patient when the ears of the guide are positioned in the piriform fossa.

A second surface also extends longitudinally in the passage and from the first surface at a predetermined angle with respect to the outer reference surface so as to cradle and protect the transverse arytenoid of the trachea. These two surfaces form a common edge with a curved configuration in the passage of the elongated member. It is this particular edge that is disposed in the passage anterior of the cricoid cartilage when the ears of the guide are positioned in the piriform fossa.

The guide also includes a tongue disposed about and extending longitudinally from the distal end of the elongated member. The tongue has a top surface communicating with the passage at a third predetermined angle with respect to the outer reference surface. This top or third surface of the tongue also communicates with and extends from the second surface and is inclined with respect to the outer reference surface so as to advantageously position the tongue in the esophagus of the patient. The tongue is also shaped for conformance with and placement in the esophagus.

The elongated member has a flexible proximal portion that is positioned about the proximal end thereof for readily advancing an intubation tube to the guiding surfaces of the elongated member.

BRIEF DESCRIPTION OF THE DRAWING

FIG. 2 depicts a partially sectioned side view of the tracheal guide of FIG. 1 inserted through the mouth and in the airway of a patient with the distal end of the guide positioned just proximal to the glottic opening of the trachea;

FIG. 3 depicts a partially sectioned side view of the tracheal guide of FIG. 2 fully inserted in the patient's airway and positioned about the glottic opening of the trachea;

DETAILED DESCRIPTION

Figure 1:
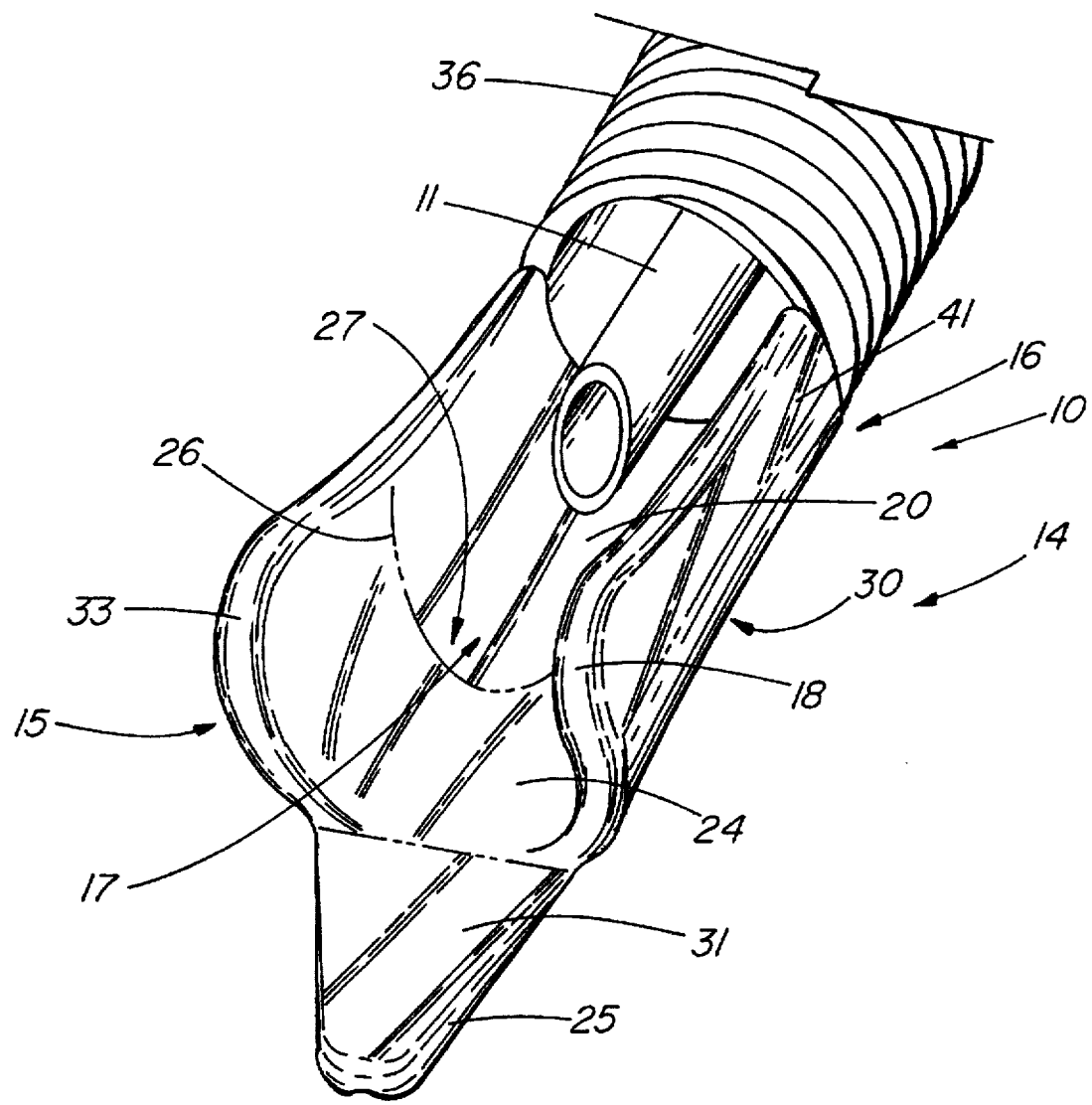
FIG. 1 pictorially depicts a preferred, illustrative embodiment of the present invention and, in particular, a tracheal guide for positioning a medical device in the trachea of a human patient.

FIG. 1 pictorially depicts a preferred, illustrative embodiment of a tracheal guide 10 for positioning a medical device 11 such as an endotracheal or intubation tube in the trachea of a human patient. The guide includes an elongated member 14 of preferably silicone or rubber or any other atraumatic, elastomeric or moldable material that can be readily molded or shaped. The guide further includes a flexible proximal portion 36 that is attached to and extending proximally from proximal end 16 of the elongated member. The elongated member is inserted into the airway passage of the human patient and positioned about the glottic opening of the trachea by lodging first and second ears 18 and 33 of the elongated member into the piriform fossa, which are located on either side of the trachea near the glottic opening. The flexible proximal portion is attached in a well-known manner to the proximal end of the elongated member and is a flexible, commercially available, medical grade tube that can be reinforced for inserting and positioning the elongated member into the airway passage of the patient.

The elongated member 14 of the tracheal guide has an outer reference surface 30 extending longitudinally and externally there along, a distal end 15, a proximal end 16, and a generally U-shaped passage 17 extending longitudinally therethrough for passage of medical device 11. First and second ears 18 and 33 are disposed laterally about distal end 15 of the elongated member and are shaped for conformance with and placement in the piriform fossa that are located laterally on either side of the trachea about the glottic opening. A first surface 20 extends longitudinally in the passage of the elongated member and is inclined at a first predetermined angle with respect to outer reference surface 30. The first surface extends from proximal end 16 of the tip portion and is inclined toward distal end 15 of the member in a direction anterior of the cricoid cartilage of the patient when the ears of the guide are positioned in the piriform fossa. This positioning of first surface 20 facilitates accurate and almost foolproof positioning of an endotracheal or intubation tube into the trachea of the patient.

To further facilitate positioning of the elongated member in the patient's airway, a second surface 24 extends longitudinally in passage 17 from first surface 20 towards distal end 15 of the elongated member. Second surface 24 extends from first surface 20 at a second predetermined angle with respect to outer reference surface 30 so as to receive and cradle the transverse arytenoid about the glottic opening of the trachea. As a result, an edge 26 with a curved configuration 27 is formed in passage 17 between the two inclined surfaces. As previously suggested, first surface 20 is inclined in a direction to extend anterior of the cricoid cartilage. Furthermore, edge 26 is also disposed in passage 17 anterior of the cricoid cartilage when the guide is positioned in the airway of the patient and, in particular, when ears 18 and 33 of the guide are positioned in the piriform fossa.

As depicted in the drawings, elongated member 14 of the tracheal guide has a plurality of surfaces or facets 41 that intersect or come in tangential contact with each other to form the overall contour of the guide. The intersection or tangential contact of these surfaces are illustrated in the drawings by phantom lines. These intersections may or may not be readily apparent to the viewer upon casual viewing of the elongated member. However, each surface or facet of the elongated member is often blended into another adjacent surface in forming the overall contour of the elongated member.

Tracheal guide 10 also includes a tongue 25 disposed about and extending longitudinally from distal end 15 of elongated member 14. Tongue 25 includes a third surface 31 which communicates with passage 17 and, in particular, second surface 24 at a third predetermined angle with respect to outer surface 30. Extending from the distal end of the elongated member, tongue 25 is inclined with respect to outer reference surface 30 and shaped for conformance with and placement in the esophagus. The tongue is tapered toward its tip so as to provide easy insertion of the guide through the airway passage of the patient and into the esophagus. Preferably, the tongue is approximately 2 cm in length; however, the tongue can be extended to approximately 6 cm to follow better the posterior pharynx into the esophagus. When ears 18 and 33 are positioned in the piriform fossa, tongue 25 is positioned in the esophagus and further orients and secures first surface 20 in a direction anterior of the cricoid cartilage. As is also apparent from the drawing, tongue 25 is also disposed between first and second ears 18 and 33 with third surface 31 extending from second surface 24, which is also positioned between ears 18 and 33.

FIGS. 2 and 3 depict partially sectioned, side views of tracheal guide 10 of FIG. 1 variously positioned in airway passage 38 of a patient 13. FIG. 2 depicts tracheal guide 10 inserted through the mouth of the patient and in the airway passage with elongated member 14 just proximal to glottic opening 39 of trachea 12. Tongue 25 is positioned in the airway passage so as to extend into esophagus 32 when ears 18 and 33 of the guide are positioned in piriform fossa 19 and 34, respectively.

FIG. 3 depicts tracheal guide 10 inserted into airway passage 38 with elongated member 14 positioned about the glottic opening of trachea 12. Tongue 25 is positioned in esophagus 32 posterior to cricoid cartilage 23. Ear 18 is positioned and conforms to piriform fossa 19. When so positioned by, for example, a medical technician, a medical device 11 such as an endotracheal or intubation tube can be easily and confidently inserted into and positioned in trachea 12.

Figure 4:
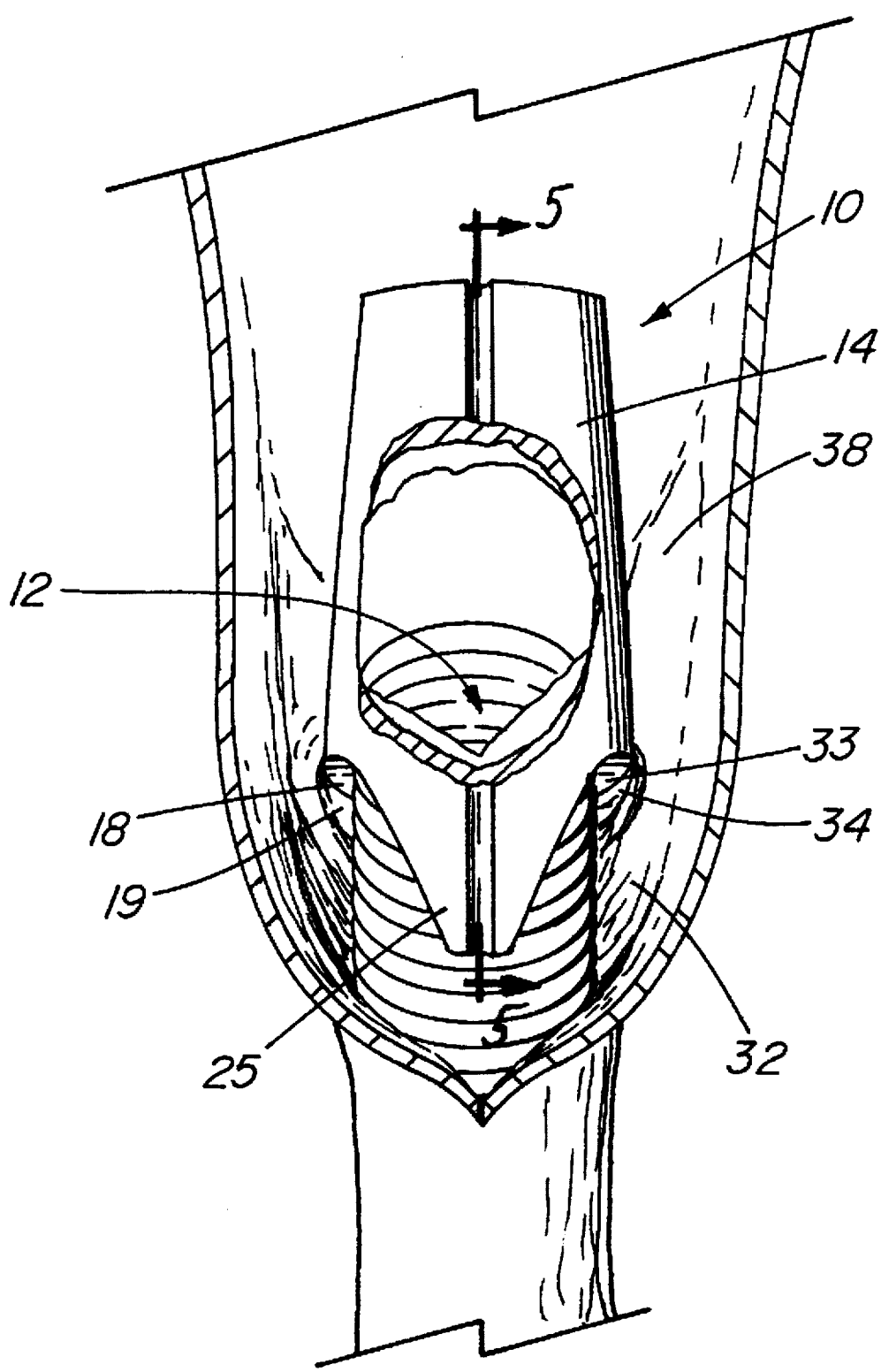
FIG. 4 depicts a partially sectioned posterior view of tracheal guide of FIG. 3 fully positioned in the patient's airway about the glottic opening of the trachea.

FIG. 4 depicts a partially sectioned and enlarged posterior view of tracheal guide 10 of FIG. 3 positioned in airway passage 38 of the patient. Tongue 25 of the guide is positioned in esophagus 32 of the patient posterior to trachea 12 with ears 18 and 33 of the guide positioned in piriform fossa 19 and 34, respectively.

Figure 5:
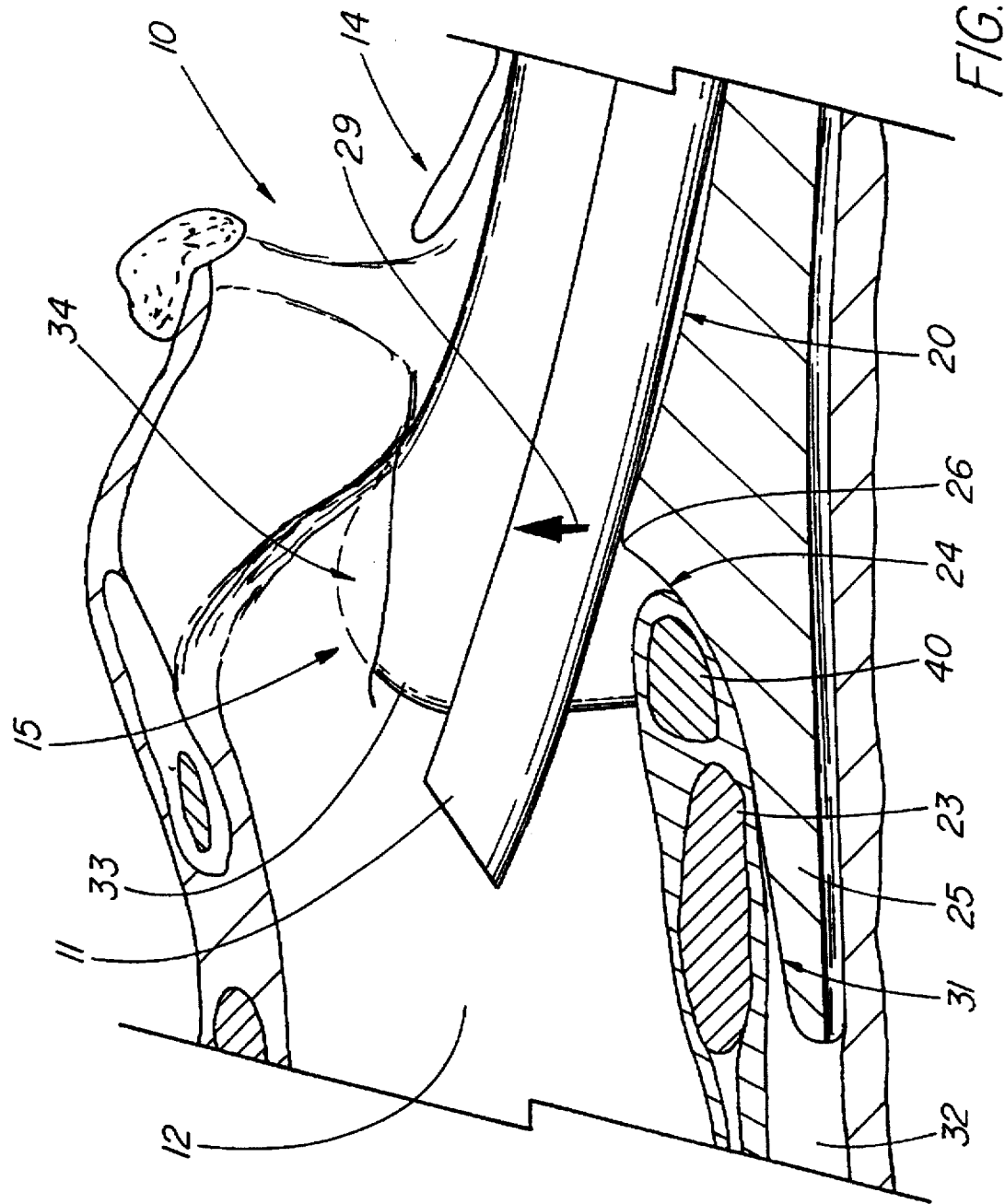
FIG. 5 depicts a longitudinally sectioned, side view of the tracheal guide of FIG. 4 taken along the line of 5—5.

FIG. 5 depicts a longitudinally sectioned view of tracheal guide 10 of FIG. 4 taken along the line of 5—5. Tongue 25 of the guide is positioned in esophagus 32 with second and third surfaces 24 and 31 positioned posterior to cricoid cartilage 23 and transverse arytenoid 40. Second passage surface 24 abuts and cradles transverse arytenoid 40 posteriorly with edge 26 positioned anterior thereof. First passage surface 20 of the guide is inclined toward distal end 15 of the elongated member and in direction 29 anterior to the cricoid cartilage and transverse arytenoid. Elongated member 14 is positioned as shown with ear 33 positioned in piriform fossa 34. When so positioned, first passage surface 20 guides and directs a medical device 11 such as an endotracheal or intubation tube, directly and atraumatically into trachea 12 of the patient.

Figure 6:
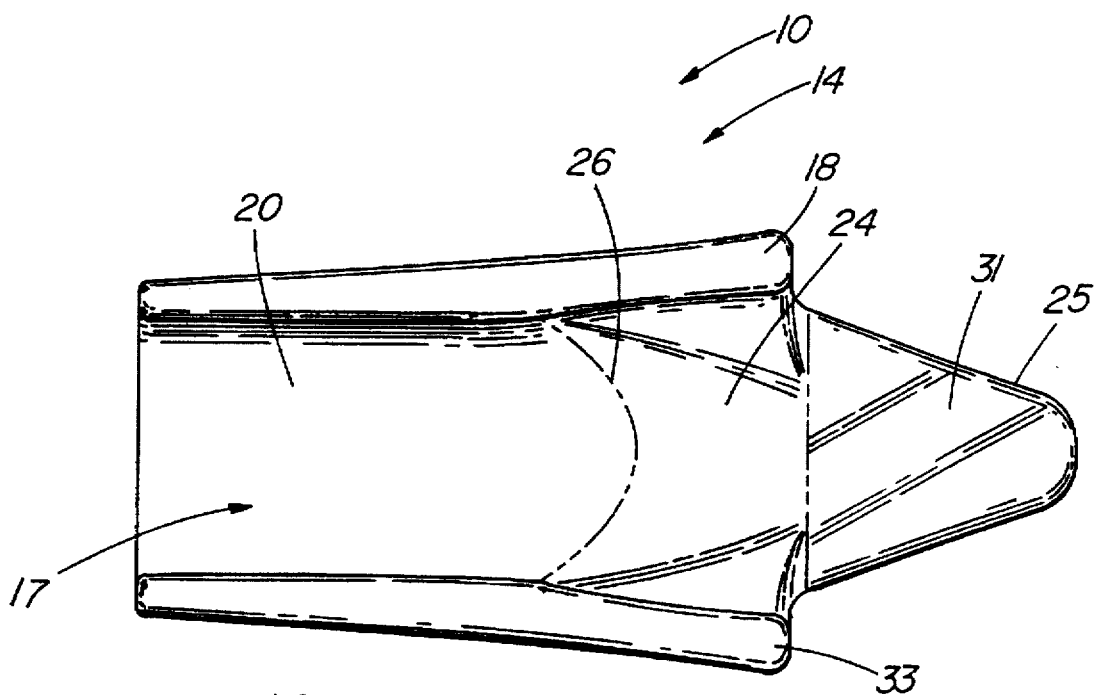
FIG. 6 depicts a top view of the tracheal guide of FIG. 1 and, in particular, the preformed tip portion thereof.

FIG. 6 depicts a top view of tracheal guide 10 of FIG. 1 and, in particular, elongated member 14. Elongated member 14 is a generally U-shaped channel with passage 17 extending longitudinally therethrough. Tongue 25 is disposed about and extends longitudinally from distal end 15 of elongated member 14. First and second surfaces 20 and 24 are positioned on the bottom of the generally U-shaped passage 17 with edge 26 therebetween. Tongue surface 31 communicates with passage 17 and extends from second passage surface 24. First and second ears 18 and 33 are disposed lateral of passage surfaces 20 and 24 and about distal end 15 of the member. Tongue 25 is V-shaped with a blunt, atraumatic distal end. Guide ears 18 and 33 are flared out for positioning in the piriform fossa of the patient.

Figure 7:
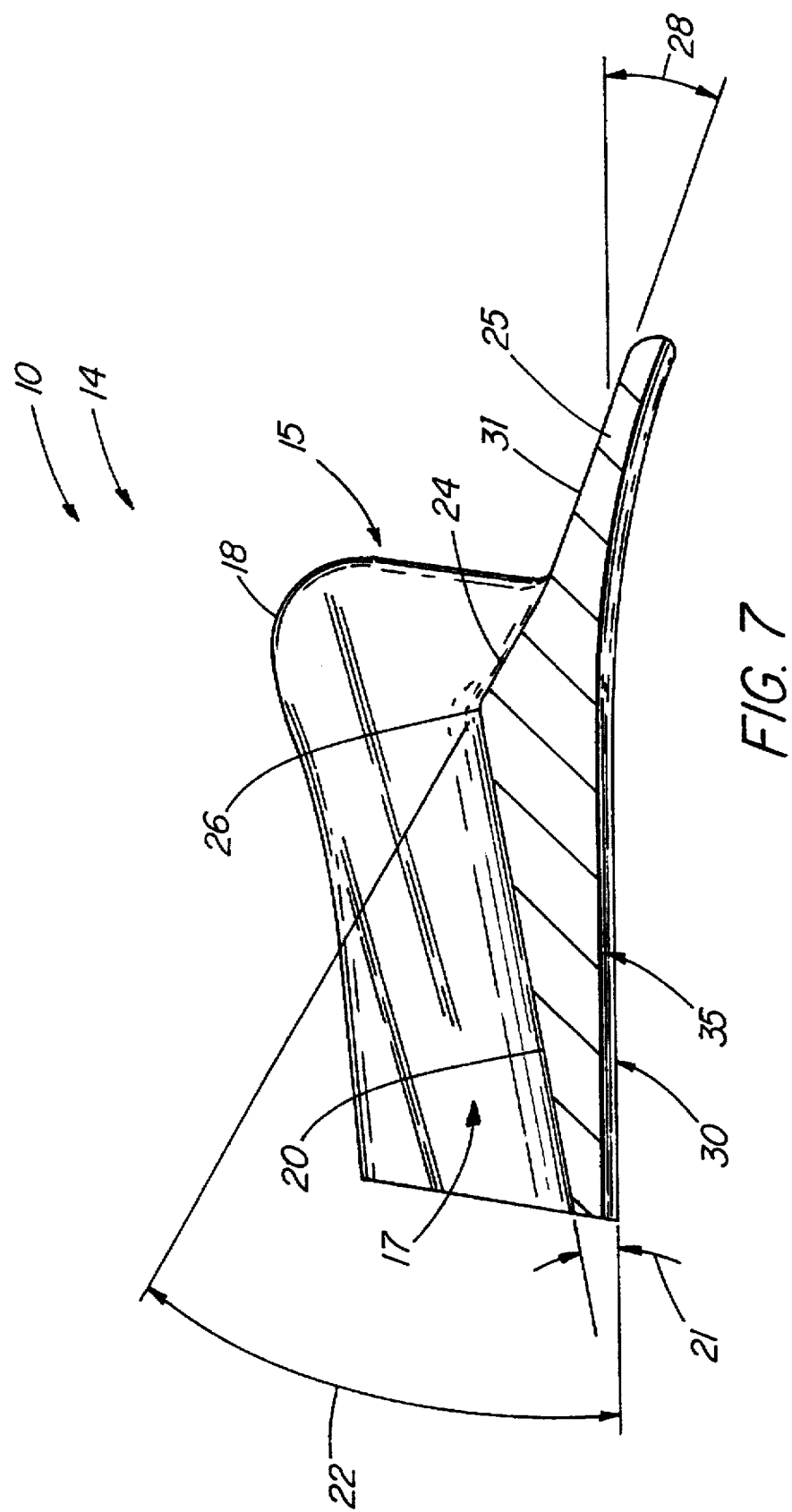
FIG. 7 depicts a sectioned side view of the tracheal guide of FIG. 6 taken along the line 7—7.

FIG. 7 depicts a longitudinally sectioned side view of tracheal guide 10 of FIG. 6 taken along the line 7—7. Elongated member 14 has a lower outer reference surface 30 of which recessed channel 35 extends longitudinally therein along the length of the member and tongue 25. Recessed channel 35 can also be enclosed and is used for positioning the guide, for example, over a suction tube already positioned in the esophagus of the patient. Alternatively, the recessed channel can be used for positioning a suction tube into the patient's esophagus for aspirating the patient's stomach. Outer surface 30 of the elongated member 14 is also used to reference the inclined position of guide surfaces 20, 24 and 31. In particular, first passage surface 20 is inclined at angle 21 such as, for example, 10 degrees with respect to outer reference surface 30. Angle 21 can range from 5 to 25 degrees. Second passage surface 24 extends in a downward direction toward distal end 15 at second angle 22 such as 40 degrees with respect to outer reference surface 30. Second angle can range from 20 to 65 degrees. First and second angles 21 and 22 are selected so as to positioned edge 26 anterior to the cricoid cartilage and transverse arytenoid. Angle 21 inclines first surface upward toward distal end 15 so as to guide a medical device directly into the trachea of the patient. Second angle 22 is selected for second surface 24 to cradle the transverse arytenoid. Second surface 24 as depicted has a slight curvature blending into third tongue surface 31. Third, tongue surface 31 forms a third angle 28 such as 20 degrees with respect to outer reference surface 30. Third angle can range from 10 to 45 degrees. First through third surface angles 21, 22 and 28 have been selected as previously indicated to position elongated member 14 about the glottic opening of the patient's trachea when ears 18 and 33 of the guide are positioned in the piriform fossa. These angles have also been selected to accommodate most adult patients. By way of example, elongated member 14 of the tracheal guide is approximately 2.5 inches long overall with tongue 25 being approximately 0.75 inches long. The overall width of elongated member 14 is approximately 1.375 inches, whereas the overall height is approximately 1.5 inches. The width of passage 17 is approximately 0.875 inches. Again, the segmented lines indicate edges of the faceted surfaces in passage 17 of the device.

Figure 8:
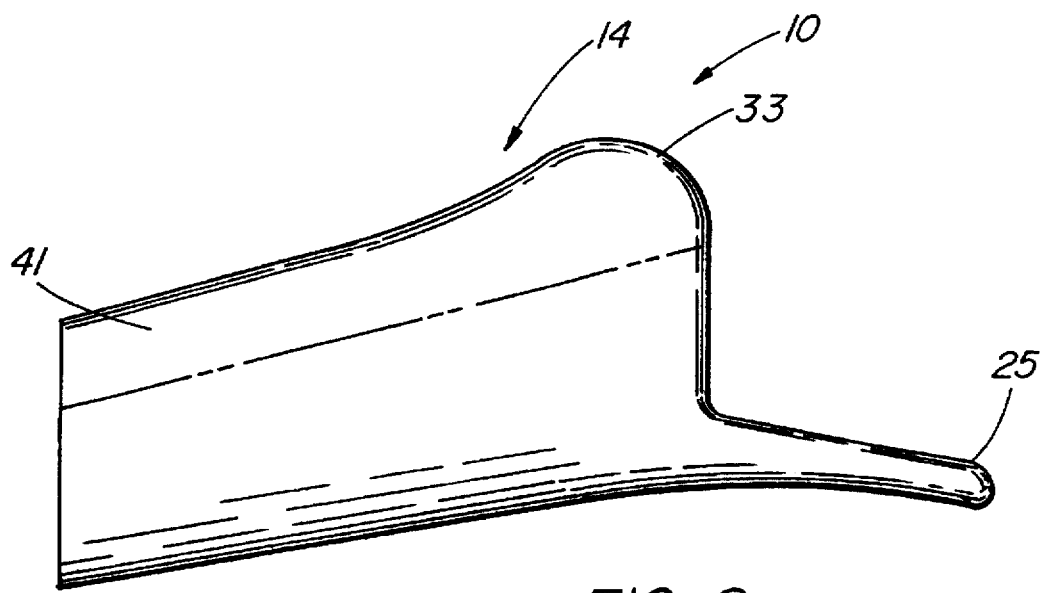
FIG. 8 depicts a side view of the tracheal guide of FIG. 1.

FIG. 8 depicts a side view of tracheal guide 10 and, in particular, elongated member 14 of FIG. 1. The phantom lines depict faceted outside surfaces 41 of member 14 and tongue 25.

Figure 9:
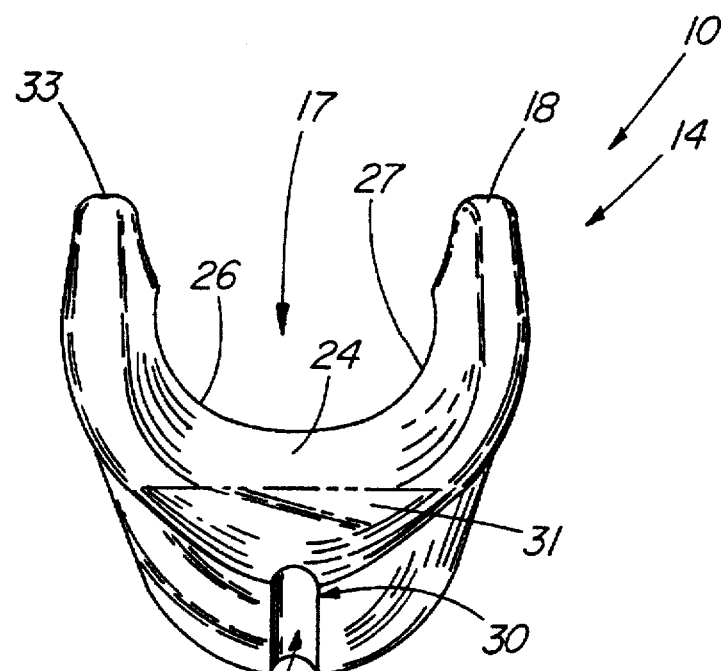
FIG. 9 depicts a front end view of the tracheal guide of FIG. 1.

FIG. 9 depicts a front end view of tracheal guide 10 and, in particular, elongated member 14 of FIG. 1. This front end view further illustrates the relationship of the faceted surfaces of the guide and, in particular, guide surfaces 24 and 31 that communicate with each other and extend from edge 26 in passage 17. The generally U-shaped configuration of passage 17 is illustrated with guide ears 18 and 33 being positioned about distal end 15 of the elongated member. Curved configuration 27 of edge 26 along with recessed channel 35 and outer reference surface 30 is also more clearly depicted.

Figure 10:
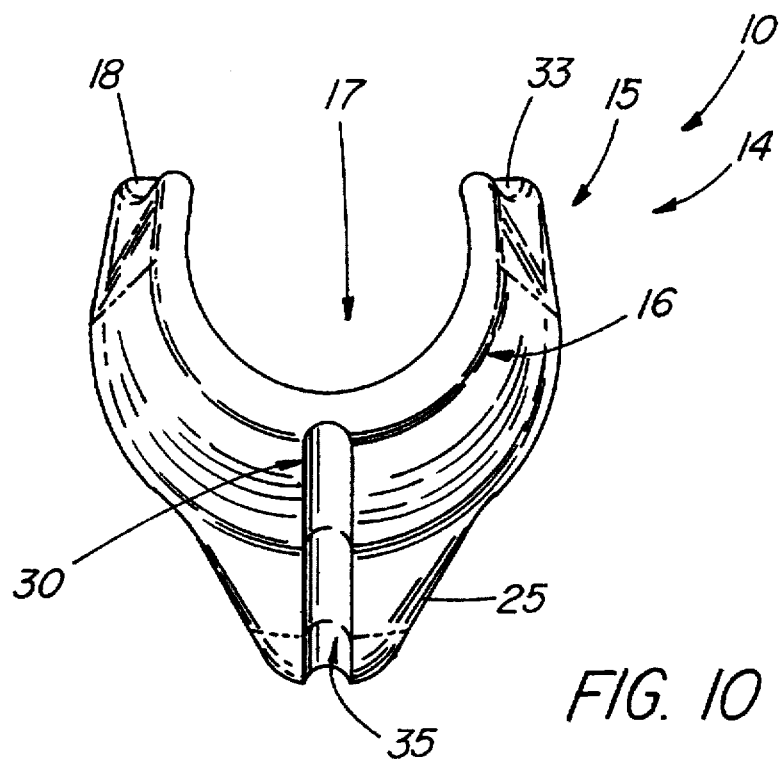
FIG. 10 depicts a rear end view of the tracheal guide of FIG. 1.

FIG. 10 depicts a rear end view of tracheal guide 10 and, in particular, elongated member 14 of FIG. 1. Generally U-shaped passage 17 is depicted extending from proximal end 16 toward distal end 15 where ears 18 and 33 are disposed thereabout. Recessed channel 35 extends the entire length of elongated member 14 in outer reference surface 30 and the bottom surface of tongue 25.

It is to be understood that the above-described tracheal guide for positioning a medical device such as an endotracheal or intubation tube in a trachea in a human patient is merely an illustrative embodiment of the principles of this invention and that other tracheal guides may be devised by those skilled in the art from without departing from the spirit and the scope of this invention. In particular, the faceted guide surfaces can be changed in forming the overall contour of the guide. As a result, the indicated angles of first, second and third surfaces with respect to the outer reference surface can be also varied so as to direct a medical device positioned in the passage of the elongated member in a direction anterior to the cricoid cartilage and transverse arytenoid. The altering of these angles and associated surfaces would be to guide a medical device directly and atraumatically into the glottic opening of the patient.

It is also contemplated that the tongue extending distally from the elongated member can be reshaped or even eliminated for particular medical applications. Alternatively, the length of tongue can be extended at least two or three times to facilitate insertion along the posterior pharynx and into the esophagus. It is further contemplated that the generally U-shaped configuration of the elongated member can also be fully enclosed. It is contemplated that the preformed portion of the elongated member is molded with at least an elastomeric moldable material for ease of manufacturing; however, other materials may be used that can be readily molded or shaped by conventional manufacturing techniques.

What is claimed is:

1. A tracheal guide (10) for positioning a medical device (11) in a trachea (12) of a human patient (13), comprising:
   an elongated member (14) having an outer reference surface (30) extending longitudinally there along, a distal end (15), a proximal end (16), and a passage (17) extending longitudinally therethrough;
   a first ear (18) disposed about said distal end (15) of said member (14) and shaped for conformance with and placement in a first piriform fossa (19) of a human patient (13); and
   a first surface (20) extending longitudinally in said passage (17) and inclined at a first predetermined angle (21) with respect to said outer reference surface (30).

2. The guide of claim 1 wherein said first surface (20) is inclined toward said distal end (15) of said elongated member (14) and in a direction (29) anterior of a cricoid cartilage (23) of the patient (13) when said first ear (18) is positioned in the first piriform fossa (19) of the patient (13).

3. The guide of claim 1 further comprising a second surface (24) extending longitudinally in said passage (17) and from said first surface (20) at a second predetermined angle (22) with respect to said outer reference surface (30).

4. The guide of claim 3 wherein said first and said second surfaces (20,24) have an edge (26) therebetween in said passage (17).

5. The guide of claim 4 wherein said edge (26) has a curved configuration (27) in said passage (17).

6. The guide of claim 4 wherein said edge (26) is disposed in said passage (17) anterior of a cricoid cartilage (23) of the patient (13) when said first ear (18) is positioned in the first piriform fossa (19) of the patient (13).

7. The guide of claim 1 further comprising a tongue (25) disposed about and extending longitudinally from said distal end (15) of said elongated member (14).

8. The guide of claim 7 wherein said tongue (25) has a third surface (31) communicating with said passage (17) at a third predetermined angle (28) with respect to said outer reference surface (30).

9. The guide of claim 8 further comprising a second surface (24) extending longitudinally in said passage (17) and from said first surface (20) at a second predetermined angle (22) with respect to said outer reference surface (30) and wherein said third surface (31) of said tongue (25) communicates with and extends from said second surface (24).

10. The guide of claim 7 wherein said tongue (25) is inclined with respect to said outer reference surface (30) and shaped for conformance with and placement in an esophagus (32) of the patient (13).

11. The guide of claim 7 further comprising a second ear (33) disposed about said distal end (15) of said elongated member (14) and shaped for conformance with and placement in a second piriform fossa (34) of the human patient (13).

12. The guide of claim 11 wherein said tongue (25) is disposed between said first and said second ears.

13. The guide of claim 7 further comprising includes a recessed channel (35) extending longitudinally in said outer reference surface (30).

14. The guide of claim 1 further comprising includes a flexible portion (36) disposed about said proximal end (16) of said elongated member (14).

15. A tracheal guide (10) for positioning a medical device (11) in a trachea (12) of a human patient (13), comprising:

an elongated member (14) having an outer reference surface (30) extending longitudinally there along, a distal end (15), a proximal end (16), and a passage (17) extending longitudinally therethrough;

a first surface (20) extending longitudinally in said passage (17) at a first predetermined angle (21) with respect to said outer reference surface (30); and a first (18) and a second (33) ear disposed laterally about said first surface (20) and said distal end (15) of said elongated member (14) and shaped for conformance with and placement in a first (19) and a second (34) piriform fossa of a human patient (13), respectively.

16. The guide of claim 15 further comprising a second surface (24) extending longitudinally in said passage (17) and from said first surface (20) at a second predetermined angle (22) with respect to said outer reference surface (30).

17. The guide of claim 16 further comprising an edge (26) between said first (20) and said second (24) surfaces and disposed in said passage (17) anterior of a cricoid cartilage (23) of the patient (13) when said first (18) and said second (33) ears are positioned in the first (19) and the second (34) piriform fossa of the patient (13), respectively.

18. The guide of claim 16 further comprising a tongue (25) disposed about and extending longitudinally from said distal end (15) of said elongated member (14), having a third surface (31) communicating with said second surface (24) at a third predetermined angle (28) with respect to said outer reference surface (30), and shaped for conformance with and placement in an esophagus (32) of the patient (13).

19. The guide of claim 15 further comprising a flexible portion (36) disposed about said proximal end (16) of said elongated member (14) and a recessed channel (35) in said outer reference surface (30).

20. A tracheal guide (10) for positioning a medical device (11) in a trachea (12) of a human patient (13), comprising:

an elongated member (14) having an outer reference surface (30) with a recessed channel (35) extending longitudinally there along, a distal end (15), a proximal end (16) and a passage (17) extending longitudinally therethrough;

a flexible portion (36) disposed about and extending longitudinally from said proximal end (16) of said elongated member (14);

a first surface (20) extending longitudinally in said passage (17) at a first predetermined angle (21) with respect to said outer reference surface (30);

a second surface (24) extending longitudinally in said passage (17) and from said first surface (20) at a second predetermined angle (22) with respect to said outer reference surface (30);

a first (18) and a second (33) ear disposed about said distal end (15) of said member (14) and laterally about said first (20) and said second (24) surfaces and shaped for conformance with and placement in a first (19) and a second (34) piriform fossa of the human patient (13), respectively;

a tongue (25) disposed about and extending longitudinally from said distal end (15) of said elongated member (14) and also disposed between said first (18) and said second (33) ears, having a third surface (31) extending from said second surface (24) at a third predetermined angle (28) with respect to said outer reference surface (30) and shaped for conformance with and placement in an esophagus (32) of the patient (13); and an edge (26) between said first (20) and said second (24) surfaces having a curved configuration (27) and disposed in said passage (17) anterior of a cricoid cartilage (23) of the patient (13) when said first (18) and said second (33) ears are positioned in the first (19) and the second (34) piriform fossa of the patient (13), respectively.

* * * * *